United States Patent [19]

Willam

[11] 4,363,238
[45] Dec. 14, 1982

[54] DEVICE FOR MEASURING THE BREATH OF PATIENTS

[76] Inventor: Franz Willam, Haubenschlossstrasse 17, D-8960 Kempten, Fed. Rep. of Germany

[21] Appl. No.: 177,375

[22] Filed: Aug. 12, 1980

[30] Foreign Application Priority Data

Aug. 16, 1979 [DE] Fed. Rep. of Germany ....... 2933116

[51] Int. Cl.³ ............................ G01F 1/68; A61B 5/08
[52] U.S. Cl. ...................................... 73/204; 128/724; 128/725
[58] Field of Search ................. 128/724, 725; 73/204, 73/188, 189; 340/606

[56] References Cited

U.S. PATENT DOCUMENTS

| | | | |
|---|---|---|---|
| 3,147,618 | 9/1964 | Benson | 73/204 |
| 3,535,927 | 10/1970 | Mahon et al. | 73/204 |
| 3,592,055 | 7/1971 | Dorman | 73/204 X |
| 3,595,079 | 7/1971 | Grahn | 73/204 |
| 3,677,085 | 7/1972 | Hayakawa | 73/204 |
| 3,900,819 | 8/1975 | Djorup | 73/204 X |
| 3,962,917 | 6/1976 | Terada | 128/725 X |
| 4,024,761 | 5/1977 | Djorup | 73/204 |
| 4,206,638 | 6/1980 | Djorup | 73/204 X |

OTHER PUBLICATIONS

Günkel, A. et al., "A Shielded Hot-Wire Probe..." Ind. Eng. Chem. Fund., vol. 10, No. 4, 1971 pp. 627-631.

Primary Examiner—Kyle L. Howell
Assistant Examiner—John C. Hanley
Attorney, Agent, or Firm—Offner & Kuhn

[57] ABSTRACT

In a device for measuring the breath volume of patients, a pair of temperature sensitive sensors are arranged in a tube-like housing of a respiration conduit of a respirator. The sensors are spaced from one another in flow direction and an air resistance member is arranged between them in such way that at least in one of the opposite air flow directions one of the sensors is in a position sheltered from the air flow by the air resistance member. Both of the sensors are connected with electronic circuits respectively and a current supply for holding the temperatures of the sensors on constant high levels. A calorimeter unit is connected to the circuits measuring the current supply necessary to compensate the temperature decrease of the sensors caused by the cool respiration flow. The air throughput is calculated in dependence on the measured current supply. Because in a predetermined flow direction the leeward sensor with respect to the air resistance member needs a lower current supply than the upstream sensor the calculating device provides different outputs for the pair of sensors whereby the flow direction can be determined and only the expiration air volume is indicated.

2 Claims, 6 Drawing Figures

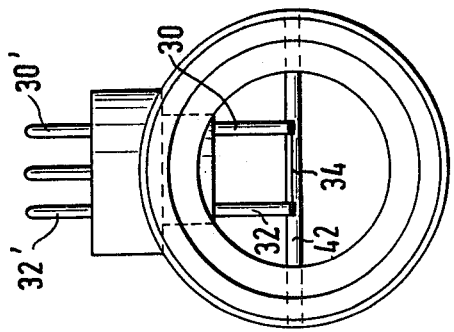
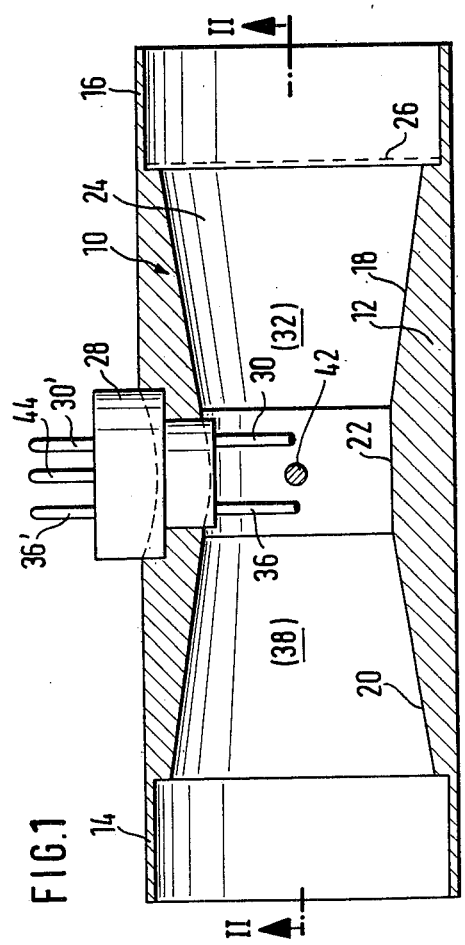
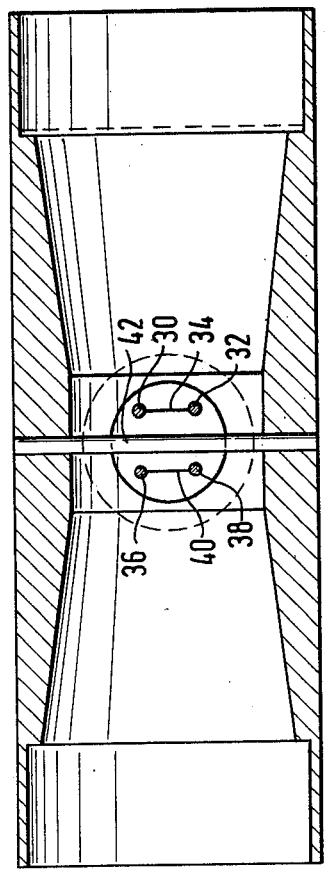

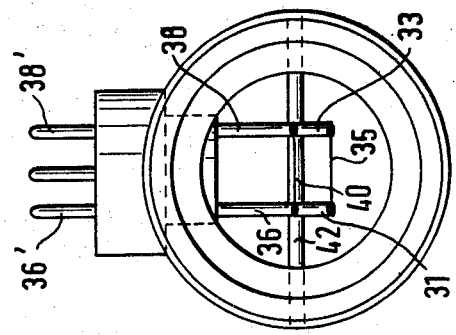
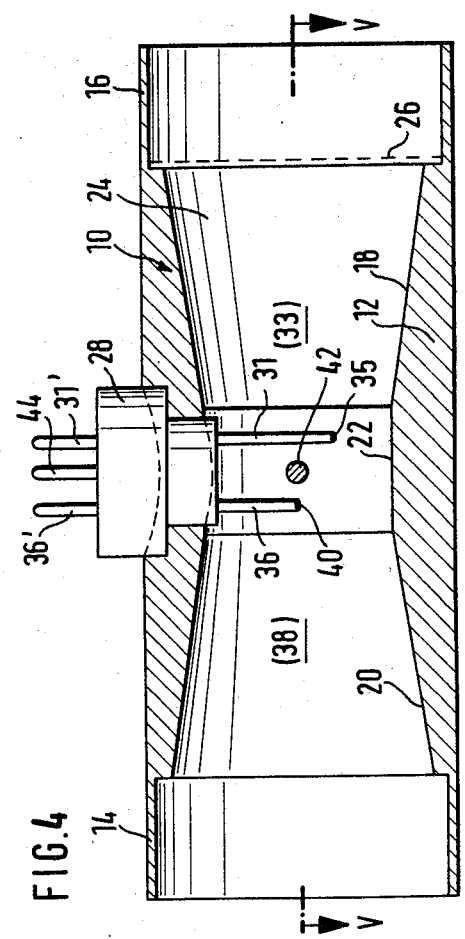
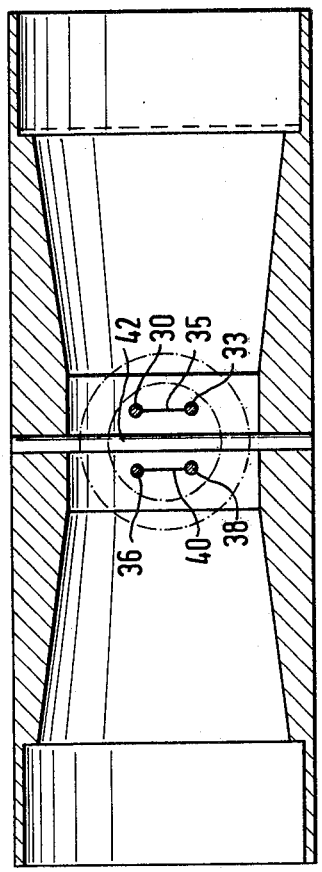

DEVICE FOR MEASURING THE BREATH OF PATIENTS

BACKGROUND OF THE INVENTION

The present invention relates to a device for measuring the breath of patients comprising measuring means arranged in a respiration conduit and provided with a sensor arranged in the air flow, the sensor being electrically connected with an electric and/or electronic circuit for holding its temperature on a constant value above the respiration temperature, a calorimeter unit measuring the current supply for compensating a momentary temperature decrease of the sensor because of the respiration air flow and a calculating and indicating device indicating the respiration air throughput in dependence on the current supply.

Known measuring devices of this kind have the disadvantage that the device cannot determine the flow direction of the respiration.

Therefore it is one object of the invention to provide a new measuring device which in a simple manner can decide whether the measured respiration dates belong to an expiration or an inspiration phase.

A further object of this invention is to provide a simple device having low-cost electronic circuits measuring the current supply for holding the sensor arrangement on a constant temperature level but indicating only the expiration phases of the patient.

A still further object of the invention is to provide a measuring device indicating the rate and the direction of a breath flow, the breath draw volume, the volume per minute, the inspiration and expiration periods and the breath frequency of respirated patients.

SUMMARY OF THE INVENTION

The new measuring device measuring the breath of patients and containing the features disclosed at the beginning comprises a tube-like housing, a second sensor arranged within said housing and provided with an own control circuit for its temperature constancy, both said sensors being arranged in axially spaced radial planes of said housing, an air resistance member spaced from each of said radial planes and arranged in such manner that in at least one of the opposite air flow directions always at least one of the pair of sensors lies in lee of the air resistance member.

According to one embodiment of the invention, both of the sensors and the air resistance member are arranged in the same axial plane of the housing. The windward sensor uses more heating energy than the leeward sensor in order to maintain the predetermined high temperatures in the region of 800 degrees Celsius, because the flowing cool air retracts more energy from the non-protected upstream sensor than from the downstream sensor sheltered by the air resistance member. The current supplies of each of the sensors are separately measured in the calorimeter units and compared with one another by a simple electronic comparator circuit. The output signal of which can be positive or negative dependent on the flow directions of the respiration air. In most cases only the expiration air of the patient is to be indicated. The new measuring device according to this invention provides a simple way to elect only the signals corresponding to the expiration phases.

According to a second embodiment, it is provided that one of said sensors and the air resistance member are situated in a common axial plane and the other one of said sensors is radially spaced from said axial plane by an amount sufficient for not being influenced by the air flow deflections caused by the air resistance member. By this arrangement a still higher accuracy of measuring is achieved, because the second sensor not at all being influenced by the air resistance member provides for absolutely exact and reproducible measurements of air flow volumes. The first sensor alternately lies on the windward side and on the leeward side of the air resistance member corresponding to the inspiration and expiration phases. When it is on the leeward side the difference signal of the comparator circuit of both sensors is substantially the same as in the first embodiment. It has a relatively high positive value. But when the first sensor is on the windward side the difference signal between the sensors remains positive but has a much lower value. This difference lies above 0, because also in the windward position of the first sensor the neighboured air resistance member deflects the air flow upstream whereby a small influence results with respect to a lower cooling effect of the first sensor.

According to the invention, the sensors consist of thin platinum wires and due to their low heat capacity provide for a substantially inertialess controlling process.

Further features and advantages of the invention are disclosed in the following description of examples.

BRIEF DESCRIPTION OF THE DRAWINGS

FIG. 1 shows a longitudinal vertical section of one embodiment of the measuring device;

FIG. 2 shows a longitudinal horizontal section along line 2—2 of FIG. 1;

FIG. 3 shows a front view of the measuring device of FIG. 1;

FIG. 4 shows a longitudinal vertical section of a second embodiment;

FIG. 5 shows a longitudinal horizontal section along line 5—5 of FIG. 4; and

FIG. 6 shows a front view of the measuring device as seen from the left side of FIG. 1.

DESCRIPTION OF THE PREFERRED EMBODIMENTS

A measuring device 10 consists of a tube-like housing 12 having cylindrical end portions 14, 16, a conical contracting portion 18, and a conical enlarging portion 20. Between the conical portions 18, 20 a cylindrical portion 22 is provided which forms the narrowest zone of a flow channel 24.

The flow channel 24 is connected via portion 14 to a respirator conduit (not shown) and via portion 16 to a conduit leading to the patient. A screen 26 protects a sensor arrangement in the cylindrical portion 22 during the expiration phase of the patient from foreign matters. The convergent-divergent nozzle of the flow channel 24 together with the narrow middle portion 22 provides for a laminar flow character of the air streams.

In the narrow middle portion 22 of the housing 12 a crossbore is provided into which an insulated insert member 28 is removably fastened, carrying a first pair of holding arms 30, 32 extending in a first radial plane and a second pair of holding arms 36, 38 extending in second radial plane spaced from the first plane. The ends of the holding arms, in the embodiment of FIGS. 1 to 3, lie in the same axial plane containing the tube axis of the housing. The ends of the first pair of holding arms 30, 32 are connected by a first sensor in form of a thin platinum wire 34. An equally formed second sensor 40 is electrically connected with the pair of second arms 36, 38. The arms are conductive, extend through the non-conductive insert member and their outer ends form contact pins 30', 32' and 36', 38' respectively for a plug-in socket.

Between the pair of platinum wires 34, 40 and spaced therefrom an air resistance rod or bar 42 extends in parallel direction to the wires. The ends of the bar 42 are fitted in the housing 12. The cross-section of the bar or rod 42 is much larger than that of the thin wires 34, 40 and the distance in flow direction is small enough so that in each of the opposite flow directions one of the sensors 34, 40 lies in lee from the air resistance bar 42 and thereby is sheltered from the air flow.

A fifth contact pin 44 is excentrically fastened at the member 28 ensuring the correct orientation of the plug-in socket.

Each pair of contact pins 30', 32' and 36', 38' is electrically connected (not shown) with a known electronic control circuit connected with a current supply and a calorimeter unit measuring the energy supply. The control circuits hold the temperatures of the platinum wires 34, 40 on a predetermined high level of substantially 800° C. Such temperature constancy control circuits are known and need not be explained in detail.

In case of an inspiration phase the air flows from the left to the right side (FIG. 1). The sensor 40 substantially not influenced by the air resistance bar 42 is remarkably cooled by the air stream but due to the operation of the control circuit for temperature constancy a momentary amount of heat is supplied to the sensor 40 which is equal with the momentary heat amount absorbed by the air stream, which in turn is in a fixed relation to the flow volume of the air stream. The calorimeter unit counts the current supply for the sensing and heating wire 40 and a value is indicated corresponding to the air throughput of the inspiration phase.

Because the other sensing and heating wire 34 is sheltered from the air flow by the bar 42 it is less cooled than the wire 40 and its control circuit has to supply less heating energy. A calculating device in form of a comparator circuit compares both the supply outputs and gives a positive difference signal, indicating an inspiration process of the patient.

Because in most cases only the expiration phase is to be calculated and indicated the calculating device suppresses all measuring signals coming from the calorimeter units if the difference signal is positive. In the expiration phase however the relations are inverted and the wire 34 is more heated than the wire 40, a negative difference signal is produced and the measured heat supply of the wire 34 is indicated as the expirations volume of the patient.

FIGS. 4 to 6 show a similar measuring device. The only difference consists in that instead of holding arms 30, 32 longer holding arms 31, 33 for a sensor 35 are used, extending beyond the axial plane which contains the other sensor 40 and the bar 42. Therefore, the sensor 35 is always situated in a position not influenced by the air resistance bar 42. This arrangement is advantageous if highest precision of measuring the expiration and/or inspiration volumes is desired. Because of the sinusoidal dependency of the momentary and air flow rates in the flow channel 24 on the time period during the respiration phases the flow patterns before and behind the bar 42 alter. That means very small differences in the flow pattern can exist at the windward sensor 35 or 40 resulting in different energy supplies and therefore in different volume indications. If the sensor 35 according to FIGS. 4 to 6 is situated outside of any influence of the flow pattern of the air created by the air resistance bar 42 or the other sensor 40 absolutely exact and reproducible measurements of the respiration volumes are warranted. In order to find the flow direction also the difference signals are used as explained above. In the expiration phase (from right to left) the difference signal between the wire 35 and the wire 40 has substantially the same large value as in the case of the wires 34 and 40. But in the opposite flow direction the signal of the windward wire 40 is indeed smaller than the signal of the wire 35 however the difference is only small. In one flow direction a large (positive) difference value is calculated and in the opposite direction a small (positive) difference value is produced. Therefore the calculating circuit can clearly distinguish the flow directions.

What I claim is:

1. An improvement in a fluid flow measuring apparatus for detecting direction of flow and the magnitude thereof, the apparatus comprising a conduit, a pair of temperature sensors arranged in the conduit, a flow resistance member arranged between radial planes of said pair of temperature sensors and axially aligned with one of said pair of temperature sensors and means for tending to maintain the temperature of each sensor at a predetermined high level above the temperature of the fluid, the improvement comprising an arrangement in which the other one of said pair of temperature sensors is radially offset with respect to the axial alignment plane intersecting the one temperature sensor and said flow resistance member.

2. An improvement as claimed in claim 1, wherein the conduit includes a pair of conical tube portions and a cylindrical tube portion therebetween, and wherein a bore is provided in the circumferential wall of the cylindrical tube portion and an insulated insert is removably arranged in said bore, the insert supporting said pair of sensors.

* * * * *